United States Patent [19]

Waddill et al.

[11] Patent Number: 4,629,769

[45] Date of Patent: Dec. 16, 1986

[54] 4,4,6-TRIMETHYLHEXAHYDROPYRIMIDINE AS AN EPOXY CURING AGENT

[75] Inventors: Harold G. Waddill; George P. Speranza, both of Austin, Tex.

[73] Assignee: Texaco Inc., White Plains, N.Y.

[21] Appl. No.: 781,598

[22] Filed: Sep. 30, 1985

[51] Int. Cl.$^4$ .............................................. C08G 59/50
[52] U.S. Cl. .................................... 525/504; 528/118; 528/361; 528/407
[58] Field of Search ................ 525/504; 528/118, 361, 528/407

[56] References Cited

U.S. PATENT DOCUMENTS

| | | | |
|---|---|---|---|
| 3,883,532 | 5/1975 | Begland | 260/256.4 C |
| 4,146,714 | 3/1979 | Alink | 544/242 |
| 4,212,843 | 7/1980 | Alink | 252/390 |
| 4,265,803 | 5/1981 | Soma et al. | 528/118 X |
| 4,289,869 | 9/1981 | Zengel et al. | 528/118 X |

*Primary Examiner*—Earl Nielsen
*Attorney, Agent, or Firm*—Jack H. Park; Kenneth R. Priem; Richard A. Morgan

[57] ABSTRACT

4,4,6-trimethylhexahydropyrimidine is partially reacted with a polyepoxide to form a room temperature Stable "B" stage epoxy resin system. This system may be stored at or near 25° C. for long periods of time without further reaction. Heating of the partially cured material rapidly transforms the B-Stage product into a crosslinked material which is both temperature and chemically resistant.

These properties make the product useful as preimpregnates with laminae such as cloth, paper, glass cloth and the like and for filament windings.

3 Claims, No Drawings

4,4,6-TRIMETHYLHEXAHYDROPYRIMIDINE AS AN EPOXY CURING AGENT

BACKGROUND OF THE INVENTION

1. Field of the Invention

This invention relates to curable epoxy resin compositions. More particularly it relates to 4,4,6-trimethylhexahydropyrimidine as a curing agent.

2. Description of the Prior Art

Epoxy resins constitute a broad class of polymeric materials having a wide range of physical characteristics. The resins are characterized by epoxide groups which are cured by reaction with certain catalysts or curing agents to provide cured epoxy resin compositions with certain desirable properties. Conventional curing agents include such compounds as polyamines, polycarboxylic acids, anhydrides and Lewis acids.

Preimpregnates are formed by partially curing a polyepoxide. The partially reacted epoxy system is stabilized before complete curing by means such as refrigeration. The partially reacted material may be formed into a required shape, with for example a filament, and the cure completed with heating.

U.S. Pat. Nos. 4,146,714 and 4,212,843 describe the synthesis of 4,4,6-trimethylhexahydropyrimidine, the epoxy resin curative of the present invention.

SUMMARY OF THE INVENTION

The invention relates to an epoxy resin composition which comprises a polyepoxide and an effective curing amount of 4,4,6-trimethylhexahydropyrimidine.

The resin when partially cured is useful as a preimpregnated composite of wide utility such as field repair of aircraft.

DESCRIPTION OF THE PREFERRED EMBODIMENTS

Part A of the two part composition of the present invention comprises an epoxy base resin typically a polyepoxide. Generally, the epoxy base resin is a vicinal polyepoxide containing compound having an average of at least 1.8 reactive 1,2-epoxy groups per molecule. These polyepoxide materials can be monomeric or polymeric, saturated or unsaturated, aliphatic, cycloaliphatic, aromatic or heterocyclic, and may be substituted if desired with other substituents besides the epoxy groups, e.g., hydroxyl groups, ether radicals, aromatic halogen atoms and the like.

Preferred polyepoxides are those of glycidyl ethers prepared by epoxidizing the corresponding alkyl ethers or reacting, by known procedures, a molar excess of epichlorohydrin and an aromatic polyhydroxy compound, i.e., isopropylidene bisphenol, novolac, resorcinol, derivatives of aromatic amines, etc. The epoxy derivatives of methylene or isopropylidene bisphenols are especially preferred. The condensation product of epichlorohydrin with bisphenol A is particularly preferred.

A widely used class of polyepoxides which are useful according to the present invention includes the resinous epoxy polyethers obtained by reacting an epihalohydrin, such as epichlorohydrin, and the like, with either a polyhydric phenol or a polyhydric alcohol. Typically the epoxy resins have an average of at least 1.8 reactive, 1,2-epoxy groups per molecule. An illustrative, but by no means exhaustive, listing of suitable dihydric phenols includes 4,4'-isopropylidene bisphenol, 2,4'-dihydroxydiphenylethylmethane, 3-3'-dihydroxydiphenyldiethylmethane, 3,4'-dihydroxydiphenylmethylpropylmethane, 2,3'-dihydroxydiphenylethylphenylmethane, 4,4'-dihydroxydiphenylpropylphenylmethane, 4,4-dihydroxydiphenylbutylphenylmethane, 2,2'-dihydroxydiphenylditolylmethane, 4,4'-dihydroxydiphenyltolylmethane and the like. Other polyhydric phenols which may also be co-reacted with an epihalohydrin to provide these epoxy polyethers are such compounds as resorcinol, hydroquinone, substituted hydroquinones, e.g., methylhydroquinone, and the like.

Among the polyhydric alcohols which can be co-reacted with an epihalohydrin to provide these resinous epoxy polyethers are such compounds as ethylene glycol, propylene glycols, butylene glycols, pentane diols, bis(4-hydroxycyclohexyl)dimethylmethane, 1,4-dimethylolbenzene, glycerol, 1,2,6-hexanetriol, trimethylolpropane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyhydric thioethers, such as 2,2'-, 3,3'-tetrahydroxydipropylsulfide and the like, mercapto alcohols such as monothioglycerol, dithioglycerol and the like, polyhydric alcohol partial esters, such as monostearin, pentaerythritol monoacetate and the like, and halogenated polyhydric alcohols such as the monochlorohydrins of glycerol, sorbitol, pentaerythritol and the like.

Another class of polymeric polyepoxides which can be amine cured and are in accordance with the present invention includes the epoxy novolac resins obtained by reacting, preferably in the presence of a basic catalyst, e.g., sodium or potassium hydroxide, an epihalohydrin, such as epichlorohydrin, with the resinous condensate of an aldehyde, e.g., formaldehyde, and either a monohydric phenol, e.g., phenol itself, or a polyhydric phenol. Further details concerning the nature and preparation of these epoxy novolac resins can be obtained in Lee, H. and Neville, K., *Handbook of Epoxy Resins*, McGraw Hill Book Co., New York, 1967.

It will be appreciated by those skilled in the art that the polyepoxide compositions which are useful in the practice of the present invention are not limited to those containing the above described polyepoxides, but that these polyepoxides are to be considered merely as being representative of the class of polyepoxides as a whole.

Part B of the two part composition of the present invention comprises 4,4,6-trimethylhexahydropyrimidine as a curing agent.

The synthesis of this curing agent is described in U.S. Pat. Nos. 4,212,843 and 4,146,714 which are incorporated herein in their entirety by reference.

Generally, the synthesis comprises reaction of acetone or mesityl oxide with ammonia or ammonium hydroxide over a solid acid catalyst with 4,4,6-trimethyl-2,3,4,5-tetrahydropyrimidine recovered by distillation. This intermediate is then catalytically hydrogenated. The product mixture is extracted and the product 4,4,6-trimethylhexahydropyrimidine recovered by distillation.

The curing agent is admixed with the polyepoxide in such an amount that there is one reactive hydrogen atom in the curing component for each epoxy group in the epoxy resin component. These are known as stoichiometric quantities. The stoichiometric quantity can be calculated from the knowledge of the chemical structure and analytical data on the component. Stoichiometry unfortunately is not always calculable. For systems of the present invention, the proper amount of curative is the amount necessary to provide the best desired properties. This amount must be determined experimentally and can be accomplished by routine procedures known in the art. Generally the number of equivalents of reactive curative groups is from about 0.8 to 1.2 times the number of epoxide equivalents present in the curable epoxy resin composition, with from 0.9 to a stoichiometric amount being preferred. The exact amount of constituents in accordance with the above general requirements will depend, as mentioned, primarily on the application for which the cured resin is intended.

The admixture is a rapid setting epoxy resin system which forms a partly reacted ("B" stage) product that is stable at ordinary room temperature; about 25° C. The "B" stage product does not require refrigeration in order to stabilize the degree of cure. When needed, the partly reacted material is formed into a required shape. This may be accomplished using the epoxy resin system alone or by coating the resin on filament or on laminae such as cloth, paper, glass cloth and the like to form a preimpregnate. The preimpregnate is cured completely with heating to produce a heat and chemically resistant cross-linked product. For development of optimum achievable properties curing of the preimpregnate at elevated temperature is necessary. The curing temperature range acceptable in this invention is from about 100° C. to about 150° C. for about ½ to 4 hours.

The following Examples are illustrative of the nature of the instant invention but are not intended to be limitative thereof.

EXAMPLE 1

Solubility of Partially Reacted (B-Stage) Epoxy Resin System Cured with 4,4,6-trimethylhexahydropyrimidine and Other Amines

| Formulation (pbw):[1] | A | B | C |
|---|---|---|---|
| Epoxy resin (EEW~185)[2] | 100 | 100 | 100 |
| 4,4,6-trimethylhexahydro-pyrimidine | 24 | — | — |
| Jeffamine ® D-230[3] | — | 32 | — |
| Diethylenetriamine[4] | — | — | 11 |
| Days of storage of "B" Stage product with solubility in DMSO[5] | >60[6] | 1–2 | <1 |

[1]Formulation mixed together in 50g batches; allowed to cure under ambient conditions (~25° C. 50% relative humidity) for 24 hours before first test of solubility. pbw - weight ratios
[2]Epoxy Resin - Liquid diglycidyl ether of Bisphenol A. Epoxy equivalent weight 185.
[3]Polyetherdiamine of ~230 molecular weight of the formula $H_2NCH(CH_3)CH_2-[OCH_2CH(CH_3)]_xNH_2$ wherein x averages 2.6 (Texaco Chemical Co.).
[4]Structure: $H_2NCH_2CH_2NHCH_2CH_2NH_2$
[5]DMSO = dimethyl sulfoxide, an efficient solvent for epoxy resin systems.
[6]The product, although readily soluble in DMSO, when heated on a hot plate rapidly became hard, infusible and insoluble in solvents.

EXAMPLE 2

Stability of B-Storage Epoxy Resin System: Oxirane Content on Storage at ~25° C.

| | | A (Example 1) |
|---|---|---|
| Oxirane content, % of original | | |
| after: 24 hours, | 25° C. | 44.3 |
| 7 days, | 25° C. | 40.0 |
| 14 days, | 25° C. | 35.7 |
| 28 days, | 25° C. | 38.6 |
| 35 days, | 25° C. | 38.6 |
| 60 days, | 25° C. | 41.4 |

EXAMPLE 3

Physical Properties of Epoxy resin System Cured with 4,4,6-trimethylhexahydroprimidine

| Formulation | |
|---|---|
| Liquid epoxy resin (EEW~185) | |
| 4,4,6-trimethylhexahydropyrimidine | |
| Cure Cycle: | Cure overnight ~25° C., then 2 hours 80°, 3 hours 150° C. |
| Properties of Cured ⅛ in casting: | |
| Izod impact strength, ft.-lbs./in. | 0.11 |
| Tensile strength, psi | 10600 |
| Tensile modulus, psi | 427000 |
| Elongation at break, % | 9.0 |
| Flexural strength, psi | 17600 |
| Flexural modulus, psi | 429000 |
| HDT, °C., 264 psi/66 psi | 100/105 |
| Shore D hardness, 0–10 sec. | 76–74 |
| Compression strength at yield, psi | 12800 |
| at failure, psi | 43900 |
| % weight gain, 24 hour water boil | 4.2 |
| 3 hour acetone boil | 9.3 |
| Adhesive Properties | |
| Tensile shear strength, psi | 3900 |
| T-peel strength, pli | 4.4 |

SUMMARY OF TEST METHODS

Tensil shear strength, psi
(ASTM Standard Test Method D-1002)
T-peel strength, pli
(ASTM Standard Test Method D-1876)
Izod impact strength, ft-lb/in
(ASTM Test D-256)
Tensil strength, psi
(ASTM Test D-638)
Tensil modulus, psi
(ASTM Test D-638)
Elongation at Break, %
(ASTM Test D-638)
Flexural strength, psi
(ASTM Test D-750)
Flexural modulus, psi
(ASTM Test D-790)
Heat Deflection Temperature
HDT, °C., 264 psi/66 psi
(ASTM Test D-648)
Shore D hardness, 0–10 sec
(ASTM Test D-2240)
Compression strength at yield; at failure
(ASTM Test D-695)

The principle of the invention and the best mode contemplated for applying that principle have been described. It is to be understood that the foregoing is illustrative only and that other means and techniques can be employed without departing from the true scope of the invention defined in the following claims.

What is claimed is:

1. An epoxy resin composition comprising:
   (A) a vicinal polyepoxide having an average of at least 1.8 reactive 1,2-epoxy groups per molecule, and (B) an effective curing amount of 4,4,6-trimethylhexahydropyrimidine.

2. A room temperature stable epoxy resin system comprising the partially cured composition of:
   (A) a vicinal polyepoxide having an average of at least 1.8 reactive 1,2-epoxy groups per molecule, and
   (B) an effective curing amount of 4,4,6-trimethylhexahydropyrimidine.

3. An epoxy composition comprising the cured product of:
   (A) a vicinal polyepoxide having an average of at least 1–8 reactive 1,2-epoxy groups per molecule, and
   (B) an effective curing amount of 4,4,6-trimethylhexahydropyrimidine.

* * * * *